(12) United States Patent
Jung (10) Patent No.: US 9,101,270 B2
(45) Date of Patent: Aug. 11, 2015

(54) APPARATUS FOR CAPTURING IMAGE OF ANTERIOR PART OF IRIS AND MEDICAL MONITORING SYSTEM USING SMART PHONE

(76) Inventor: Ha-Chul Jung, Seoul (KR)

( * ) Notice: Subject to any disclaimer, the term of this patent is extended or adjusted under 35 U.S.C. 154(b) by 0 days.

(21) Appl. No.: 14/128,013

(22) PCT Filed: Oct. 11, 2011

(86) PCT No.: PCT/KR2011/007500
§ 371 (c)(1),
(2), (4) Date: Dec. 20, 2013

(87) PCT Pub. No.: WO2012/176960
PCT Pub. Date: Dec. 27, 2012

(65) Prior Publication Data
US 2014/0132932 A1   May 15, 2014

(51) Int. Cl.
| | | |
|---|---|---|
| A61B 3/10 | (2006.01) | |
| A61B 5/00 | (2006.01) | |
| A61B 3/12 | (2006.01) | |
| A61B 3/117 | (2006.01) | |
| A61B 3/14 | (2006.01) | |
| A61B 3/00 | (2006.01) | |
| A61B 5/103 | (2006.01) | |
| G06F 19/00 | (2011.01) | |
| A61B 5/107 | (2006.01) | |

(52) U.S. Cl.
CPC .............. *A61B 5/0059* (2013.01); *A61B 3/0008* (2013.01); *A61B 3/1173* (2013.01); *A61B 3/1216* (2013.01); *A61B 3/14* (2013.01); *A61B 5/0077* (2013.01); *A61B 5/1032* (2013.01); *A61B 5/1079* (2013.01); *G06F 19/3418* (2013.01); *H04M 2250/52* (2013.01)

(58) Field of Classification Search
CPC ...... A61B 3/1216; A61B 3/02; A61B 3/1225; A61B 3/12; A61B 3/1015; A61B 3/103; A61B 3/14; A61B 3/00; A61B 3/0008
USPC .................................. 351/205, 206, 221, 246
See application file for complete search history.

(56) References Cited

U.S. PATENT DOCUMENTS

| | | | |
|---|---|---|---|
| 2002/0008768 | A1 | 1/2002 | Takada et al. |
| 2005/0084179 | A1* | 4/2005 | Hanna et al. .................. 382/294 |

FOREIGN PATENT DOCUMENTS

| | | |
|---|---|---|
| JP | 2009-205576 A | 9/2009 |
| KR | 10-0335279 B1 | 5/2002 |
| KR | 10-2005-0043040 A | 5/2005 |
| KR | 10-0490082 B1 | 5/2005 |
| KR | 10-0872495 B1 | 12/2008 |

* cited by examiner

*Primary Examiner* — James Greece
(74) *Attorney, Agent, or Firm* — AKC Patents LLC; Aliki K. Collins (57) ABSTRACT

The present invention relates to an apparatus for capturing an image of the anterior part of an iris, and a medical monitoring system using a smart phone. According to the apparatus for capturing an image of the anterior part of an iris, the present invention can contribute to the health of the eyes by accurately examining or capturing images of healthy states to diseased states of an iris by precisely capturing an image without reflecting light to the iris while easily opening the eyes through a more effective and simple method, and proceeding with follow-up treatment thereto.

5 Claims, 9 Drawing Sheets

APPARATUS FOR CAPTURING IMAGE OF ANTERIOR PART OF IRIS AND MEDICAL MONITORING SYSTEM USING SMART PHONE

CROSS-REFERENCE TO RELATED APPLICATION

This application claims the benefit of Korean Patent Application No. 10-2011-0059985, filed on Jun. 21, 2011 in the Korean Intellectual Property Office, the disclosure of which is incorporated herein by reference.

DESCRIPTION

1. Technical Field

The present invention relates to an apparatus for capturing an image of an anterior part of an iris, and more particularly, to an apparatus for capturing an image of an anterior part of an iris with which it is possible to precisely capture an image of the iris without the reflected light while easily opening the eye by a more effective and simple method, it is possible to accurately determine a health condition and diagnose diseases by capturing the image of the iris, follow-up measures can be taken according to results of the determination and the diagnosis, and it is possible to conduce to eye care.

2. Background Art

In general, whether or not a body is healthy, whether or not the body suffers from a disease, and whether or not the disease is progressed have been diagnosed by detecting a change in shape or color of an iris of the eye.

Conventionally, in order to examine the iris, a doctor has examined or diagnosed the eye with the naked eye while the doctor opens an eyelid of a patient with one hand and brightly shines a flashlight on the eye with the other hand. In recent years, an eye examining device using a computer has been used.

However, when the doctor examines the eye with the naked eye as in the former, since the eye of the patient is exposed to light of the flashlight for a long time, there is a problem in that the eye of the patient gets tired. Further, there is a problem in that since the eye of the patient fills with tears due to irritation from strong light of the flashlight for a long time and light is reflected from the tears, it is difficult to precisely examine the iris. Furthermore, a research paper disclosed that direct light by a LED leads to a cataract and glaucoma has been published.

When the iris is illuminated using the computer to examine the iris as in the latter, there is a problem in that since reflected light is caused in the iris by the illuminated light, it is difficult to accurately capture an image of the iris by the computer. Further, there is a problem in that since the eye has a spherical shape, dot-shaped reflected light is necessarily caused in a portion where an optical fiber cable is directly illuminated, and since portions around the reflected light are affected by the reflected light, it is difficult to precisely capture a portion where the reflected light is caused and portions around the portion due to the reflected light when capturing the eye by the computer.

Meanwhile, systems that have been developed in the field until now have been separately operated as simple image transmitting systems or measurement information transmitting systems of various medical equipments. Since a technology using a WAN (Wide Area Network) is inadequate, information is provided to only limited areas and persons.

Particularly, the measurement information transmitting system has problems in that only limited areas are monitored by providing CCTVs (Closed Circuit Televisions) at operating rooms and intensive care units and the measurement information transmitting system is used only for educational purpose by separately providing wired cables in an auditorium when necessary and by using expensive separate equipment such as a beam projector. Moreover, the measurement information transmitting system has problems in that since a separate server needs to be set up in order to use the WAN, there is a burden of use due to initial investment cost, and inconvenience is aggravated due to separate pipes, separate wirings, and additional equipment.

On the other hand, it has been attempt to integrally operate the medical image transmitting system and the measurement information transmitting system described above, but the integrated system is merely configured to integrally combine existing equipments in a central operation room other than the integrated system using a practical network. Thus, the integrated system may be inadequacy to solve the problems.

Accordingly, there is a need for a new system capable of integrally transmitting a medical image and measured information and simultaneously using image monitored and measured information by a plurality of persons authorized through the WAN.

In order to solve the conventional problems, Korean Patent Publication No. 10-2003-001295 discloses a system in which image and audio information obtained by capturing operating scenes by a camera and measured information collected from various medical equipments such as electrocardiograph are transmitted to a remote place through a network and Internet network by using a multimedia mini server and the transmitted information is stored, so that real-time data (medical image and measured information) can be provided to a doctor in charge at a remote location and authorized persons involved to immediately check a condition of a patient and the provided information can be used as lively audiovisual educational data in a remote medical educational institution.

However, since this technology requires a remote control system, high cost and a lot of effort are needed to set up the system, and maintenance and handling of the system are not easy.

Meanwhile, as the medical equipment is recently developed, internal affected parts of the patient are captured in many cases. Examples of the medical image capturing equipment include CT, MRI, X-RAY, US, ANGIO, COLPOSCOPY, and CERVICORGRAPHY, and these equipments are widely used in internal medicine, general surgery, and obstetrics and gynecology.

Namely, in the case of a person with an affected part that cannot be seen by the eyes, that is, a patient whose bone is affected, a patient whose organ such as stomach or intestine is affected, or a serious patient whose head is wounded or is seriously ill, since a doctor cannot directly examine such a patient by using a stethoscope, hand, or eye, the affected part of the patient is captured using the medical image capturing equipment.

The captured medical image is provided to a reading doctor, and the reading doctor determines a condition of the patient on the basis of read medical image.

As stated above, when the doctor in charge of the patient determines a condition of the patient while seeing medical image data of the patient, the doctor in charge listens to opinions of the reading doctor who reads professionally the medical image data of the patient in order to more accurately determine the condition of the patient.

In this case, there is a problem in that the reading doctor who reads professionally only the medical image data visits the doctor in chare in order to describe the medical image data of the patient to the doctor in charge of the patient.

In addition, as mentioned above, since the reading doctor who reads the medical image data and the doctor in charge of the patient rearrange their schedules in order to accurately read the medical image data of the patient, the doctor in charge needs to wait according to a reading schedule of the reading doctor who reads the medical image data. For this reason, there is a problem in that unnecessary time is taken to check the condition of the patient. Accordingly, there is a need for a new alternative.

DISCLOSURE

Technical Problem

An object of the present invention is to provide an apparatus for capturing an image of an anterior part of an iris with which it is possible to precisely capture an image of the iris without the reflected light by a more effective and simple method, it is possible to accurately determine a health condition and diagnose diseases by capturing the image of the iris, follow-up measures can be taken according to results of the determination and the diagnosis, and it is possible to conduce to eye care.

In other words, since straight rounded light by the conventional optical fiber is difficult to move up to a deep position beyond a pupil, the eye is captured by inserting light spots beyond the pupil in order for LED light not to harm a retinal cell so as to be suitable for the eye (bulging eye) of an Asian or the eye (deep-set eye) of an European or an American, and health is not harmed by providing back and forth devices at both sides so as not to harm eye care.

An object of the present invention is to also provide a medical monitoring system using a smart phone with which it is possible to capture body parts anywhere without location limitations and many cables, it is convenient to transfer an image through wireless data communication by using applications of the smart phone, it is possible to use the system in an ear-nose-and-throat clinic as well as it is possible to capture the iris, the pupil, the skin and the hair when adaptors are replaced so as to enable various capturing, it is possible to the system used as a measure for healthcare, and it is possible to conduce to people' health.

Effect of the Invention

According to the present invention, it is possible to precisely capture an image of the iris without the reflected light by a more effective and simple method, it is possible to accurately determine a health condition and diagnose diseases by capturing the image of the iris, follow-up measures can be taken according to results of the determination and the diagnosis, and it is possible to conduce to eye care.

Further, according to the present invention, it is possible to capture body parts anywhere without location limitations and many cables, it is convenient to transfer an image through wireless data communication by using applications of the smart phone, it is possible to use the system in an ear-nose-and-throat clinic as well as it is possible to capture the iris, the pupil, the skin and the hair when adaptors are replaced so as to enable various capturing, it is possible to the system used as a measure for healthcare, and it is possible to conduce to people' health.

DESCRIPTION OF DRAWINGS

FIGS. 2 (*a*) and (*b*) are left side view of the apparatus shown in FIG. 1.

FIGS. 5(*a*) and (*b*) illustrate perspective views of a lower rubber ad an upper rubber.

FIGS. 9(*a*) and (*b*) illustrate various types of converters.

BEST MODE

In order to achieve the objects, there is provided an apparatus for capturing an image of an anterior part of an iris. The apparatus includes an apparatus main body (10) that accommodates various electronic device components therein and constitutes a hard case.

The apparatus further includes a dark room (11) that is provided at one side of the apparatus main body (10) to capture an image of an anterior part of an iris.

The apparatus further includes a pair of side covers (20) that forms sidewalls of the dark room (11) with the dark room (11) interposed therebetween.

The apparatus further includes a pair of light sources (21) that is provided at the pair of side covers (20), is movable back and forth by a pair of side back and forth buttons (25) provided at a top of the apparatus main body (10) or is movable back and forth by themselves, and serves as both-side illuminations at both sides when capturing the image of the anterior of the iris.

The apparatus further includes a sliding lid (30) that is disposed at tops of the pair of side covers (20), satisfies a condition of the dark room (11) by cooperating with the pair of side covers (20), and is slidably movable back and forth at the tops of the pair of side covers (20).

The apparatus further includes a camera lens (40) that is disposed at an inner central area of the dark room (11) to capture the image of the anterior part of the iris.

The apparatus further includes a switch (12) that is provided at the apparatus main body (10) to turn on or off the light sources (21).

The switch (12) may be implemented such that the light sources (21) are repeatedly operated in a low-intensity light mode, a high-intensity light mode, and an off mode whenever the switch is pressed or the light sources enter the off mode to be turned off when a predetermined time elapses.

A lower rubber (51) as a lower eyelash opening device that opens lower eyelashes while lowering the lower eyelashes may be detachably coupled to a lower end positioned lower than the dark room (11).

An upper rubber (52) as an upper eyelash opening device that opens upper eyelashes while raising the upper eyelashes may be detachably coupled to the sliding lid (30) which is an upper end positioned higher than the dark room (11).

The image of the anterior part of the iris may be precisely captured with more ease by automatically opening the lower and upper eyelashes by the lower rubber (51) and the upper rubber (52).

Meanwhile, in order to achieve the objects, there is provided a medical monitoring system using a smart phone. The system includes a smart phone case (120) that is provided with a screen (111) and a camera attachable lens (112), and is detachably coupled to one side of the smart phone (110) capable of performing wireless transmission.

The system further includes a lens (121) that is provided at the smart phone case (120);

The system further includes a pair of LED illumination units (123) that is disposed around the lens (121), and is respectively disposed at inner walls of a pair of side covers (122), which is movable back and forth or is fixed, to illuminate at both sides.

The system further includes a light source button (125) that operates the LED illumination units (123).

The system further includes an illumination-unit circuit (127) that transmits a manipulation of the light source button (125) as an operation of the LED illumination units (123).

The system further includes a battery (129) that supplies power for operating the smart phone case, the lens, the LED illumination units, the light source button, the illumination-unit circuit, and the battery.

Here, the medical monitoring system may further include various types of converts that is detachably coupled to one side of the smart phone case (120) and has light outlet paths (212 and 222). The light outlet paths may be used to align or adjust angles by side illuminations using a reflex mirror, a lens, and a optical fiber, and the converters may be able to precisely capture capturing parts including the inside of an ear, the inside of a uterus, the inside of a nose, blood, skin, and scalp with ease so as to have a three dimensional effect without reflected light.

Hereinafter, preferred embodiments of the present invention will be described with reference to the accompanying drawings.

Figure 1:
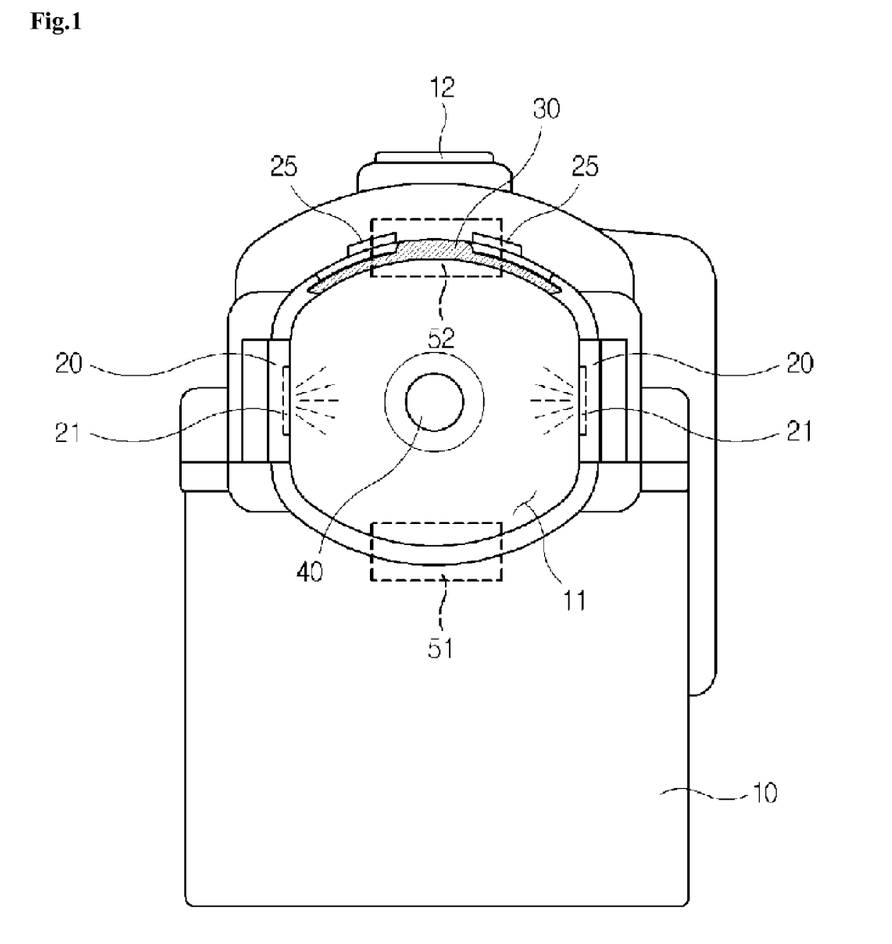
FIG. 1 is a front view of an apparatus for capturing an image of an anterior part of an iris according to an embodiment of the present invention.
Figure 2:
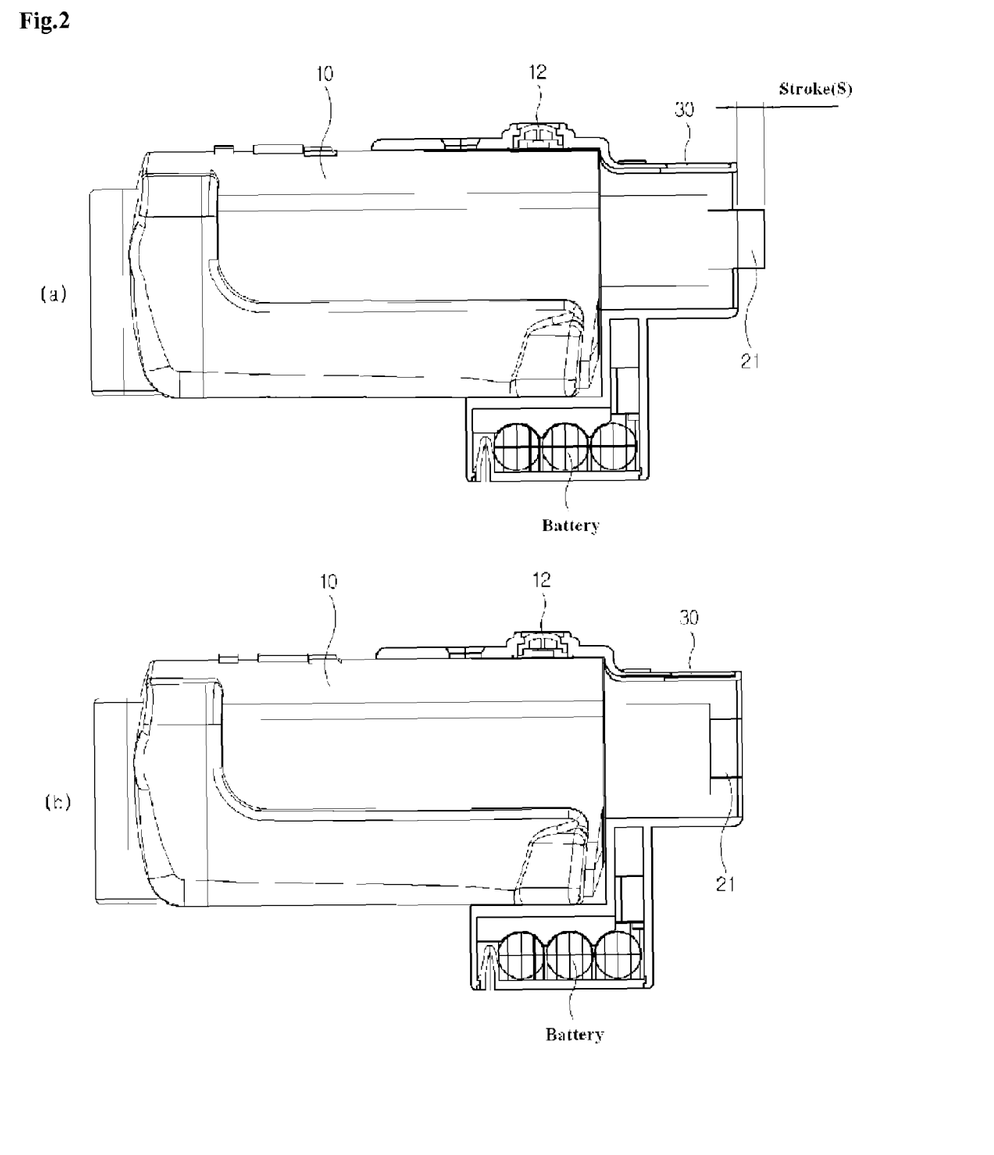
Figure 3:
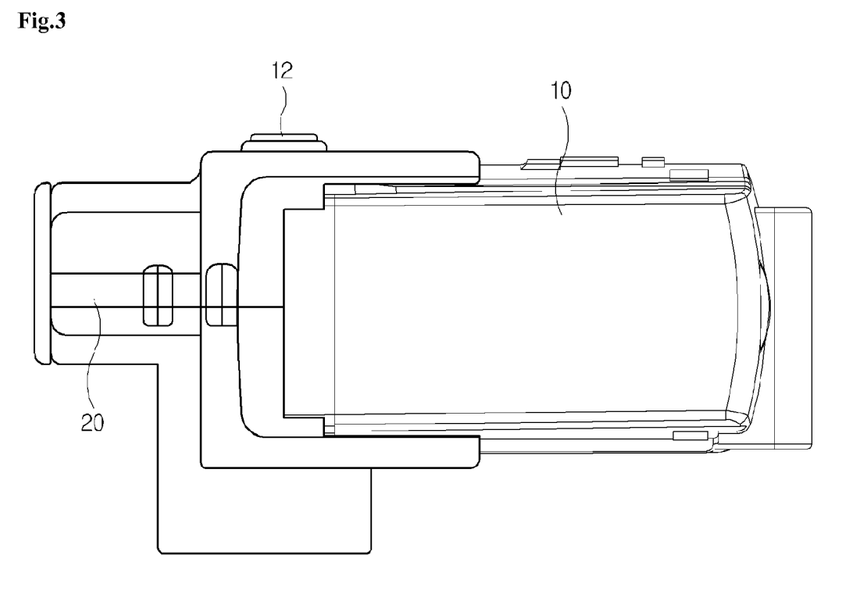
FIG. 3 is a right side view of the apparatus shown in FIG. 1.
Figure 4:
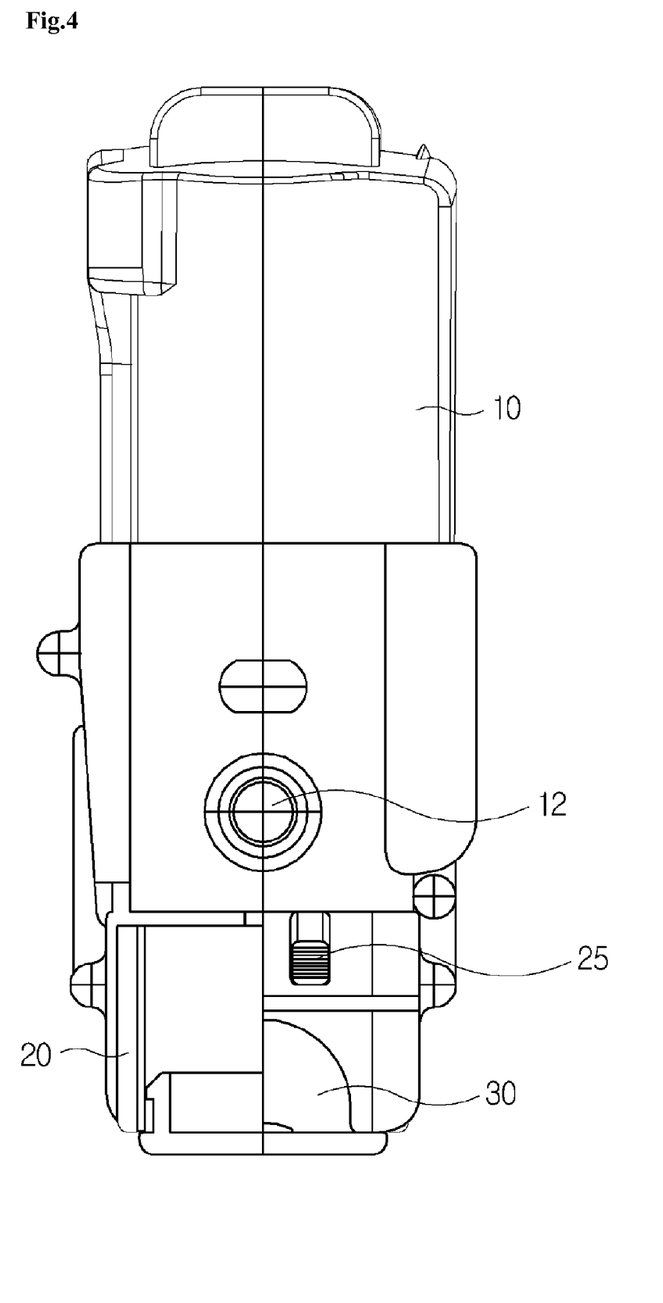
FIG. 4 is a plan view of the apparatus shown in FIG. 1.
Figure 5:
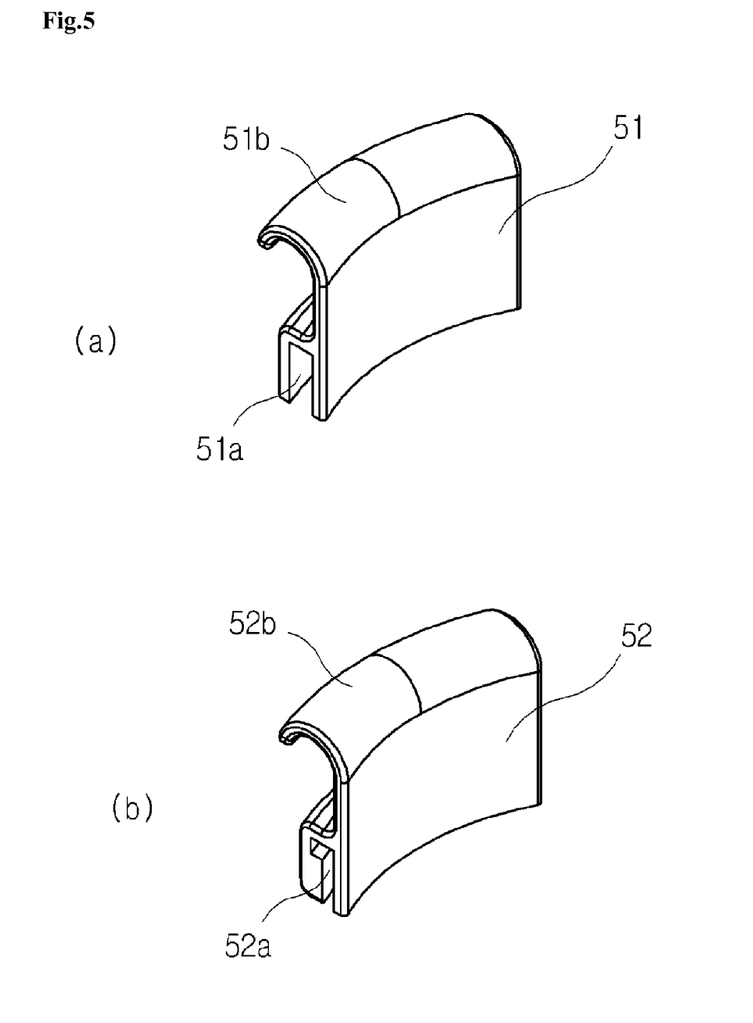
Figure 6:
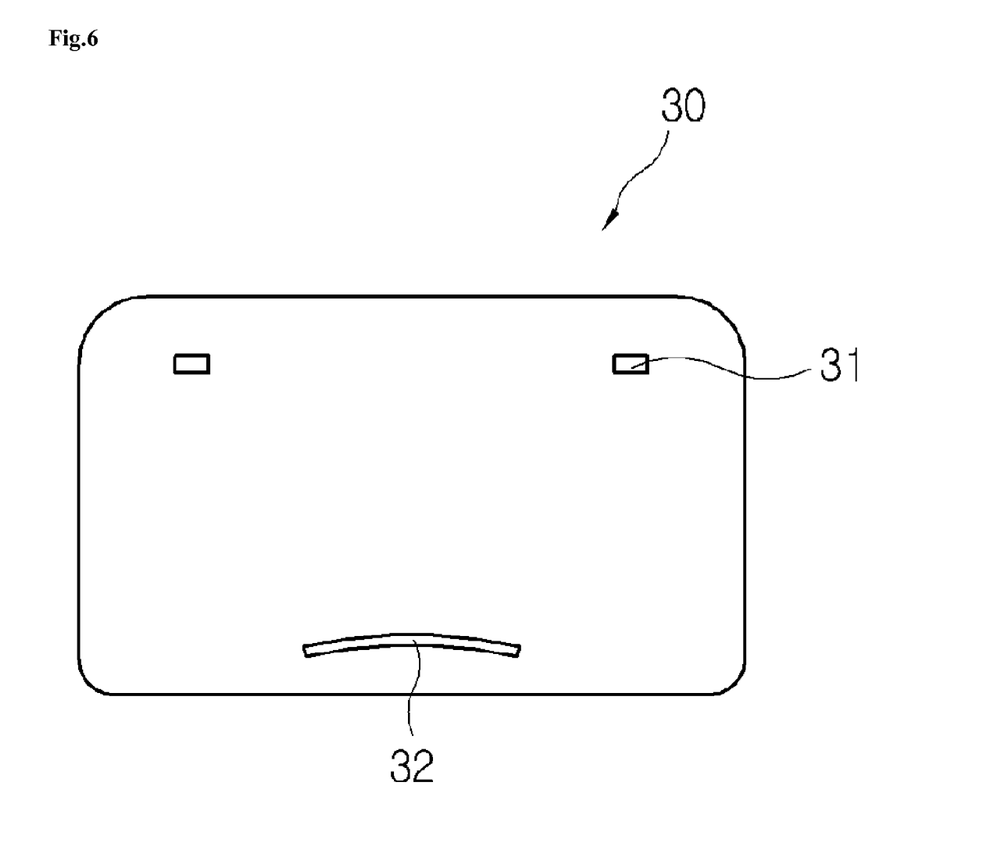
FIG. 6 is a plan view of a sliding lid.

FIG. 1 is a front view of an apparatus for capturing an image of an anterior part of an iris according to an embodiment of the present invention, FIG. 2 is a left side view of the apparatus shown in FIG. 1, FIG. 3 is a right side view of the apparatus shown in FIG. 1, FIG. 4 is a plan view of the apparatus shown in FIG. 1, FIG. 5 illustrates perspective views of a lower rubber and an upper rubber, and FIG. 6 is a plan view of a sliding lid.

An eye is divided into a pupil, an iris, and a white see of the eye, and the present invention is derived to precisely capture an image of the iris in this structure of the eye. In other words, the apparatus for capturing an image of an anterior part of an iris according to the present embodiment shown in FIGS. 1 to 4 is one compact electronic device used to capture an image of an iris. Especially, the apparatus for capturing an image of an anterior part of an iris according to the present embodiment can exhibit an excellent effect in terms of portability.

The apparatus for capturing an image of an anterior part of an iris of the present invention includes an apparatus main body 10 that accommodates various electronic device components therein and constitutes a hard case; a dark room 11 that is formed at one side of the apparatus main body 10 to capture an image of an anterior part of an iris; a pair of side covers 20 that forms both sidewalls of the dark room 11 with the dark room 11 interposed therebetween; a pair of light sources 21 that is provided at the pair of side covers 20, is movable back and forth by a pair of side back and forth buttons 25 that is provided at a top of the apparatus main body 10 or is movable by themselves, and serves as both-side illuminations at both sides when capturing the image of the anterior part of the iris; a sliding lid 30 that is disposed at tops of the pair of side covers 20, satisfies a condition of a dark room 11 by cooperating with the pair of side covers 20, and is slidably movable back and forth at the tops of the pair of side covers 20; a camera lens 40 that is disposed at an internal central area of the dark room 11 to capture the image of the anterior part of the iris; and a switch 12 that is provided at the apparatus main body 10 to turn on or off the light sources 21.

The apparatus main body 10 constitutes an exterior. The apparatus main body may be put around operator's neck with strings and may be carried by the operator. The apparatus main body 10 accommodates various electronic components therein. The camera lens 40 and the switch 12 for turning on or off the light sources 21 are provided at the apparatus main body 10.

The dark room 11 is provided at one side of the apparatus main body 10. The dark room is a space where an eye is positioned when capturing the image of the iris.

The pair of side covers 20 is walls for maintaining the dark room 11 in the dark so as to satisfy a capturing condition by cooperating with the sliding lid 30. In other words, the pair of side covers 20 and the sliding lid 30 may be external walls of the dark room 11.

Meanwhile, in the present embodiment, the pair of light sources 21 may have a stroke corresponding to a length "S" (see (a) of FIG. 2), but the pair of light sources 21 may be positioned as shown in (b) of FIG. 2.

As shown in (a) and (b) of FIG. 2, by allowing the pair of light sources 21 to be movable back and forth without being fixed, it is possible to capture an image of an iris of an American or a European whose eye is deep-set and an image of the eye of an Asian whose eye bulges without reflected light, so that it is possible to improve reliability of measured values. That is, it is possible to capture the image of the anterior of the iris while blocking external light without dazzling so as to have a three dimensional effect without reflected light.

At this time, the pair of light sources 21 may be manually slid back and forth, or may be electrically slid back and forth by using a motor. Further, the sliding lid 30 may provide the same function by sliding back and forth.

In the present embodiment, the pair of light sources 21 may be movable back and forth by manually pulling the light sources, or the pair of light sources may be movable back and forth by pushing or pulling the pair of side back and forth buttons 25 provided at the top of the apparatus main body 10.

The pair of light sources 21 is preferably both-side illuminations to give a three dimensional effect to the iris, the pupil, skin, and hair and to prevent the reflected light and the dazzling, so that it is possible to improve the reliability in capturing the image of the iris or the pupil, especially.

On the other hand, the switch 12 may be implemented such that the light sources 21 are repeatedly operated in a low-intensity light mode, a high-intensity light mode and an off mode whenever the switch is pressed or the light sources enter the off mode to be turned off when a predetermined time elapses.

For example, the pair of light sources 21 that illuminates at sides may be turned on with low intensity when the switch 12 is pressed once, the intensity of the pair of light sources may become higher than the previous intensity when the switch is pressed again, and the pair of light sources may be turned off when the switch is pressed again. Naturally, when the switch 12 is not pressed for a predetermined time, for example, about five minutes, the light sources 21 are automatically turned off, so that it is possible to prevent a battery from being wasted.

As shown in FIG. 6, the sliding lid 30 is formed substantially in a square plate shape when viewed from the top. Further, at the sliding lid 30, a pair of main-body separation preventing stoppers 31 that prevents the sliding lid from being arbitrarily separated from the apparatus main body when the sliding lid is inserted into the apparatus main body 10 and a rubber separation preventing stopper 32 that prevents an upper rubber 52 to be described below from being separated when the upper rubber is fitted are formed so as to protrude therefrom. The rubber separation preventing stopper 32 may not be easily separated by being fitted into a detachable coupling groove 52*a* of the upper rubber 52.

Referring to FIGS. 1 to 5, a lower rubber 51 that opens eyelashes while lowering the eyelashes is detachably coupled to a lower end positioned lower than the dark room 11, and the upper rubber 52 that opens eyelashes whiling raising the eyelashes is detachably coupled to an upper end positioned higher than the dark room 11.

In other words, the lower rubber 51 as a lower eyelash opening device that opens lower eyelashes while lowering the lower eyelashes is detachably coupled to the lower end positioned lower than the dark room 11, and the upper rubber 52 as an upper eyelash opening device that opens upper eyelashes while raising the upper eyelashes is detachably coupled to the sliding lid 30 which is the upper end positioned higher than the dark room 11. It is possible to precisely capture the image of the anterior part of the iris with ease by automatically opening the lower and upper eyelashes by the lower rubber 51 and the upper rubber 52.

FIG. 1 schematically illustrates the lower rubber 51 and the upper rubber 52 by dotted lines, and (a) and (b) of FIG. 5 are pictorial views of the lower rubber 51 and the upper rubber 52 that are schematically illustrated by the dotted lines in FIG. 1.

As illustrated in FIG. 5, the lower rubber 51 and the upper rubber 52 are made of a rubber material and are coupled to a lower side and an upper side of the dark room 11 as shown in FIG. 1. In such a configuration, when the present apparatus is positioned close to the eye, it is possible to further improve a capturing effect of the anterior part of the iris by naturally opening the eyelashes. The lower rubber 51 and the upper rubber 52 are detachably provided, and thus detachable coupling grooves 51*a* and 52*a* are respectively formed at the lower rubber 51 and the upper rubber 52. Since a thickness of a portion into which the lower rubber 51 is fitted is thicker than that of the other portion, the detachable coupling groove 51*a* for the lower rubber 51 is wider than the detachable coupling grove 52*a* for the upper rubber 52. Rounded portions 51*b* and 52*b* of the lower rubber 51 and the upper rubber 52 are positioned around the eyelashes to press the eyelashes so as to naturally open the eyelashes.

As described above, according to the present embodiment, it is possible to precisely capture the image of the iris without the reflected light by a more effective and simple method, so that it is possible to accurately determine a health condition and diagnose diseases by capturing the image of the iris. As a result, follow-up measures can be taken according to results of the determination and the diagnosis, so that the apparatus can conduce to eye care.

Figure 7:
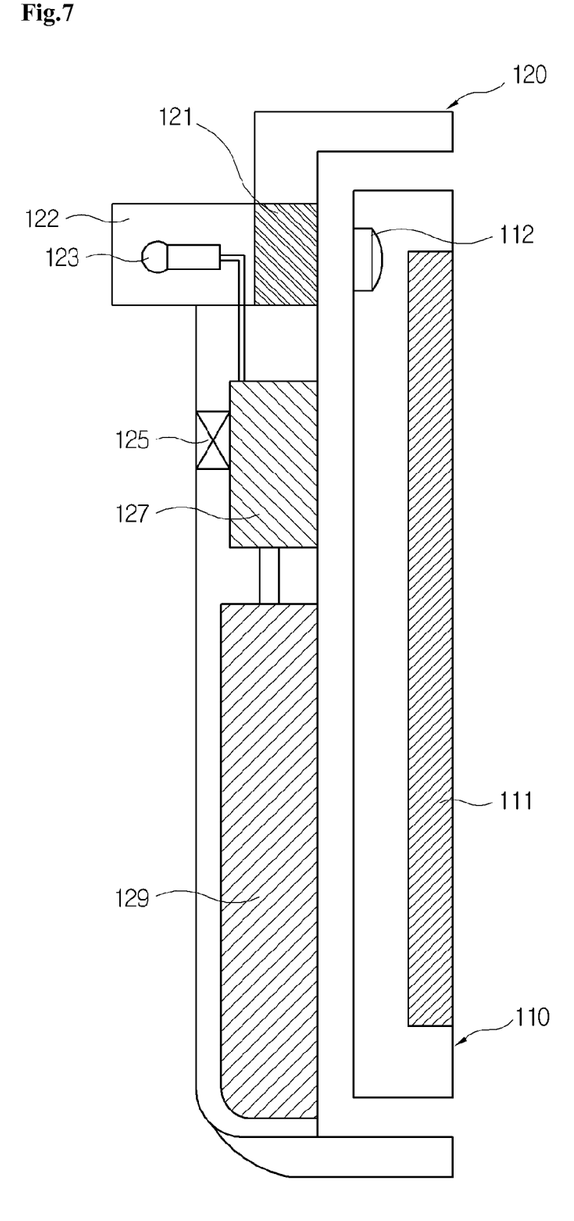
FIG. 7 is a side view of a medical monitoring system using a smart phone according to another embodiment of the present invention.
Figure 8:
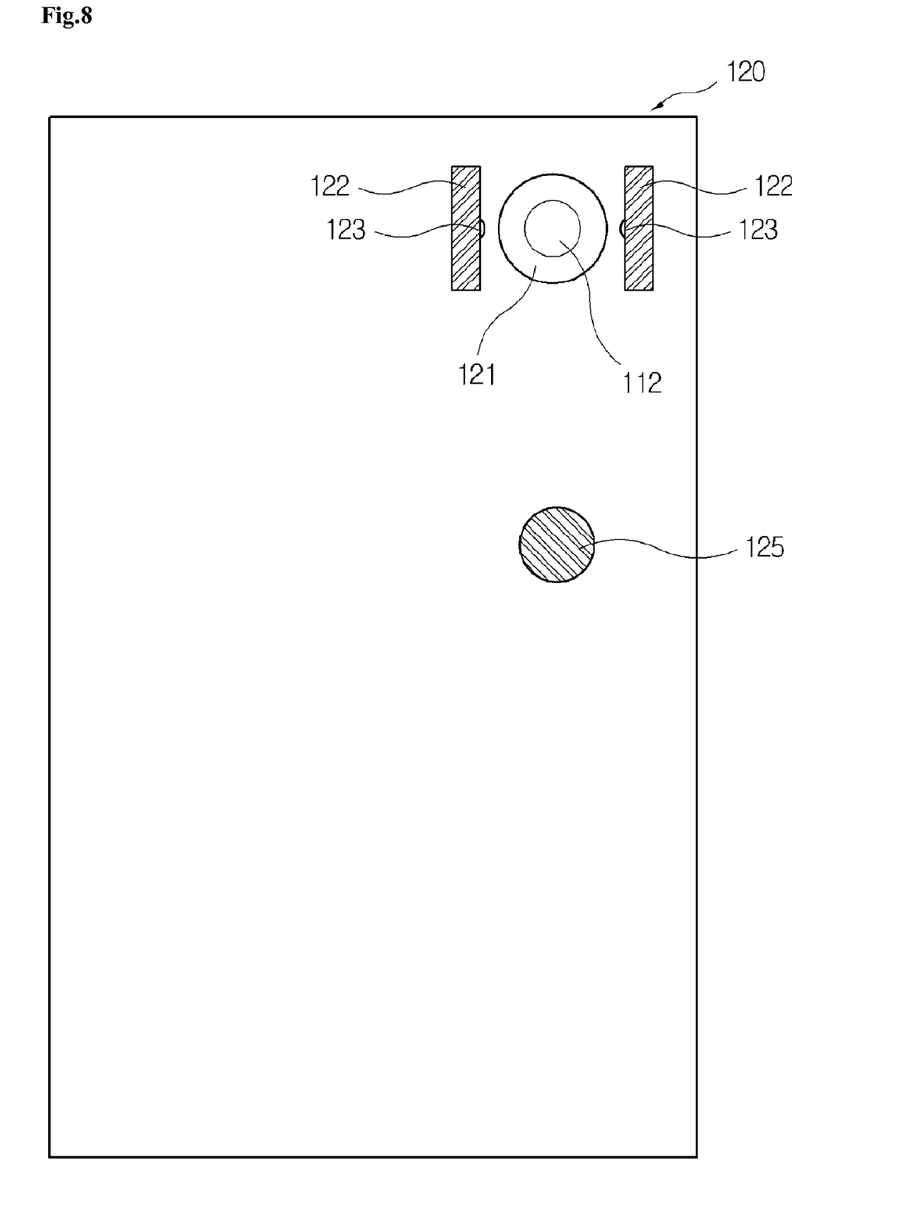
FIG. 8 is a rear view of the system shown in FIG. 7.
Figure 9:
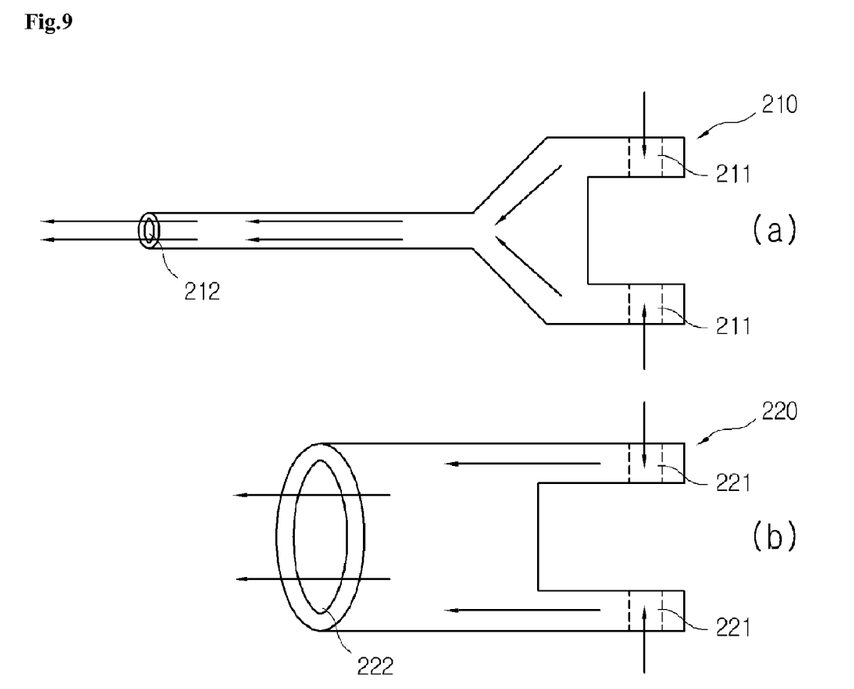

Meanwhile, FIG. 7 is a side view of a medical monitoring system using a smart phone according to another embodiment of the present invention, FIG. 8 is a rear view of the system shown in FIG. 7, and FIG. 9 illustrates various types of converters.

Since an existing medical monitoring system is connected to components such as a computer, a monitor, a camera and an illumination system through many cables, the existing medical monitoring system has a limitation of mobility and occupies a fixed location. Further, the existing medical monitoring system has a heavy cost burden.

However, in order to solve the aforementioned problems, the medical monitoring system using a smart phone according to the embodiment of the present invention is characterized in that it is possible to capture the image of the eye anywhere without location limitations and many cables by combining a smart phone case that accommodates a special lens and both-side emitting LED illumination units therein so as not to damage the eye care with a smart phone that accommodates a high pixel camera therein, it is convenient to transfer the image through wireless data communication by using applications of the smart phone, and the medical monitoring system can be used in an ear-nose-and-throat clinic as well as it is possible to capture the iris, the pupil, the skin and the hair when adaptors are replaced so as to enable various capturing.

Referring to FIGS. 7 to 9, the medical monitoring system of the present invention includes a smart phone case 120 that is provided with a screen 111 and a camera attachable lens 112 and is detachably coupled to one side of the smart phone 110 capable of performing wireless transmission; a lens 121 that is provided at the smart phone case 120; a pair of LED illumination units 123 that is disposed around the lens 121 and is respectively disposed at inner walls of the pair of side covers 122, which is movable back and forth or is fixed, to illuminate at both sides; a light source button 125 for operating the LED illumination units 123; an illumination-unit circuit 127 that transmits a manipulation of the light source button 125 as an operation of the LED illumination units 123; and a battery 129 that supplies power for operating these components.

The lens 121 may be a macro lens capable of capturing the iris or the pupil, especially.

In the present embodiment, the pair of side covers 122 may be fixed or may be moved back and forth. When the pair of side covers 122 is movable back and forth without being fixed, it is possible to capture an image of an iris of an American or a European whose eye is deep-set and an image of the eye of an Asian whose eye bulges without reflected light, so that it is possible to improve reliability of measured values. That is, it is possible to capture the image of the anterior of the iris while blocking external light without dazzling so as to have a three dimensional effect without reflected light.

At this time, the pair of side covers 122 may be manually slid back and forth, or may be electrically slid back and forth by using a motor.

The medical monitoring system of the present invention uses the smart phone 110. The smart phone 110 combines the advantages of a mobile phone with the advantages of a PDA (personal digital assistant), and adds data communication functions such as schedule management, facsimile transmission and reception, and Internet connection to the functions of the mobile phone. Unlike an existing mobile phone that is released as a finished product and uses only given functions, the smart phone has the best feature in that a user installs, adds or uninstalls several hundreds of applications as the user wants.

The smart phone has advantages which are not included in the existing mobile phone in that the user can access Internet in various manners by using various browsing programs as well as the user can directly access Internet through wireless Internet, the user can develop a desired application by himself or by herself, the user can implement interfaces suitable for the user through various applications, and the user can share the applications between other users using smart phones in which the same OS (operating system) is installed.

In Korea, LG Information and Communications Co., Ltd. and Samsung Electronics Co., Ltd. have developed smart phones that combine a microcomputer with a digital mobile phone using a CDMA (Code Division Multiple Access) method. These smart phones can be used as a portable computer, and can wirelessly conduct Internet, PC communication, and facsimile transmission while moving. Smart phones that use an analogue method, a GSM method in Europe and a PHS in Japan so as to conduct wireless communication have been developed, but the smart phones that use the CDMA method have been developed for the first time.

The two companies had released smart phones, which adopt a LCD display having a size two times larger than a screen of a typical mobile phone, transmit and receive data, and have a PIM (Personal Information Management) function capable of managing 1000 addresses to 2000 addresses, on April, 2000 at about the same time.

'SCH-M series' which are smart phones of Samsung Electronics Co., Ltd. transmit and receive data in a touch screen manner and have functions such as English-Korean dictionary, Korean-English dictionary, scientific calculator and games. Further, the 'SCH-M series' can store 2000 addresses maximally, an annual schedule, 100 memos. The 'SCH-M series' adopt a LCD having a size of 30×70 mm and have a size of 118×50×25 mm and a weight of 158 g when a standard battery is attached.

'Cyon smart phones' of LG Information and Communications Co., Ltd. can use data services such as text message, e-mail and Internet connection and have a personal information management function that integrally manages 1000 or more addresses, schedules, and memos. Furthermore, the 'Cyon smart phones' can transmit and receive data stored in a computer while being charged using a docking station. The 'Cyon smart phones' adopt a LCD having a size of 40×52 mm and have a size of 139×55×22 mm and a weight of 178 g when a standard battery is attached.

The present invention may be applied to any type of the smart phones 110.

The smart phone case 120 having the lens 121, the LED illumination units 123, the light source button 125, the illumination-unit circuit 127 and the battery 129 is attached to the smart phone 110. In such a configuration, it may be attempt to capture the image through the camera attachable lens 112 by allowing the LED illumination units 123 to be emitted at both sides through the action of the illumination-unit circuit 127 by pressing the light source button 125, and the stored image may be wirelessly transmitted to anywhere. Accordingly, the present invention is useful to capture an eye condition of the iris and various faces. The battery 129 may be attachable or fixed battery provide at the smart phone 110.

On the other hand, as shown in (a) and (b) of FIG. 9, the medical monitoring system may further use various kinds of converters to capture other body parts in addition to the face, and (a) of FIG. 9 illustrates a converter 210 for capturing the inside of an ear, the inside of a uterus and the inside of a nose, (b) of FIG. 9 illustrates a converter 220 for capturing blood, skin and scalp. Since these converters are maintained at a desired shape, that is, side light angles at circular sides or both sides, the converters can use the angle, so that it is possible to capture the body parts so as to have a three dimensional effect by using side illuminations.

In both of the converter 210 for capturing the inside of the ear, the inside of the uterus and the inside of the nose and the converter 220 for capturing blood, skin and scalp, light inlet paths 211 and 221 through which the both-side illuminations emitted from the pair of LED illumination units 123 described above are incident are formed, and light outlet paths 212 and 222 through which the both-side illuminations that have been incident and then have been combined are released are formed at positions opposite to the light inlet paths. In such a configuration, it is possible to usefully use the convert to capture the inside of the ear, the inside of the uterus and the inside of the nose or to measure and manage the blood or the skin. Especially, in FIG. 9, the light outlet paths 212 and 222 are important. It is possible to more precisely capture the body parts so as to further have the three dimensional effect by additionally providing a bowing angle adjustment device at these light outlet paths.

Although not shown, when a converter including a dark room is used, the converter can be useful to closely capture the iris of the eye in addition to the contour of the face.

As described above, according to the present invention, it is possible to capture the body parts anywhere without location limitations and many cables, and it is convenient to transfer the image through wireless data communication by using applications of the smart phone. Further, the medical monitoring system can be used in an ear-nose-and-throat clinic as well as it is possible to capture the iris, the pupil, the skin, the hair and blood when adaptors are replaced so as to enable various capturing. Accordingly, the medical monitoring system can be used as a measure for healthcare, so that the medical monitoring system can conduce to people' health.

As described above, the present invention is not to be restricted by the above-described embodiments, and it is to be appreciated that those skilled in the art can change or modify the embodiments without departing from the scope and spirit of the present invention. Therefore, the claims of the present invention are intended to cover such change and modifications.

INDUSTRIAL APPLICABILITY

The present invention can be used in the field of iris capture.

The invention claimed is:

1. An apparatus for capturing an image of an anterior part of an iris, comprising:
   an apparatus main body (10) that accommodates various electronic device components therein and constitutes a hard case;
   a dark room (11) that is provided at one side of the apparatus main body (10) to capture an image of an anterior part of an iris;
   a pair of side covers (20) that forms sidewalls of the dark room (11) with the dark room (11) interposed therebetween;
   a pair of light sources (21) that is provided at the pair of side covers (20), is movable back and forth by a pair of side back and forth buttons (25) provided at a top of the apparatus main body (10) or is movable back and forth by themselves, and serves as both-side illuminations at both sides when capturing the image of the anterior of the iris;
   a sliding lid (30) that is disposed at tops of the pair of side covers (20), satisfies a condition of the dark room (11) by cooperating with the pair of side covers (20), and is slidably movable back and forth at the tops of the pair of side covers (20);
   a camera lens (40) that is disposed at an inner central area of the dark room (11) to capture the image of the anterior part of the iris; and
   a switch (12) that is provided at the apparatus main body (10) to turn on or off the light sources (21).

2. The apparatus for capturing an image of an anterior part of an iris according to claim 1, wherein the switch (12) is implemented such that the light sources (21) are repeatedly operated in a low-intensity light mode, a high-intensity light mode, and an off mode whenever the switch is pressed or the light sources enter the off mode to be turned off when a predetermined time elapses.

3. The apparatus for capturing an image of an anterior part of an iris according to claim 1, wherein a lower rubber (51) as a lower eyelash opening device that opens lower eyelashes while lowering the lower eyelashes is detachably coupled to a lower end positioned lower than the dark room (11), an upper rubber (52) as an upper eyelash opening device that opens upper eyelashes while raising the upper eyelashes is detachably coupled to the sliding lid (30) which is an upper end positioned higher than the dark room (11), and the image of the anterior part of the iris is precisely captured with more ease by automatically opening the lower and upper eyelashes by the lower rubber (51) and the upper rubber (52).

4. A medical monitoring system using a smart phone, comprising:

- a smart phone case (120) that is provided with a screen (111) and a camera attachable lens (112), and is detachably coupled to one side of the smart phone (110) capable of performing wireless transmission;
- a lens (121) that is provided at the smart phone case (120);
- a pair of LED illumination units (123) that is disposed around the lens (121), and is respectively disposed at inner walls of a pair of side covers (122), which is movable back and forth or is fixed, to illuminate at both sides;
- a light source button (125) that operates the LED illumination units (123);
- an illumination-unit circuit (127) that transmits a manipulation of the light source button (125) as an operation of the LED illumination units (123); and
- a battery (129) that supplies power for operating the smart phone case, the lens, the LED illumination units, the light source button, the illumination-unit circuit, and the battery.

5. The medical monitoring system using a smart phone according to claim 4, further comprising:

- various types of converts that is detachably coupled to one side of the smart phone case (120) and has light outlet paths (212 and 222),
- wherein the light outlet paths are used to align or adjust angles by side illuminations using a reflex mirror, a lens, and a optical fiber, and
- the converters are able to precisely capture capturing parts including the inside of an ear, the inside of a uterus, the inside of a nose, blood, skin, and scalp with ease so as to have a three dimensional effect without reflected light.

* * * * *